(12) United States Patent
Baklanov et al.

(10) Patent No.: US 6,319,736 B1
(45) Date of Patent: Nov. 20, 2001

(54) APPARATUS AND METHOD FOR DETERMINING POROSITY

(75) Inventors: Mikhail Rodionovich Baklanov, Leuven (BE); Fedor Nikolaevich Dultsev; Konstantin Petrovich Mogilnikov, both of Novosibirsk (RU); Karen Maex, Herent (BE)

(73) Assignee: Interuniversitair Microelektronica Centrum (IMEC), Leuven (BE)

( * ) Notice: Subject to any disclaimer, the term of this patent is extended or adjusted under 35 U.S.C. 154(b) by 0 days.

(21) Appl. No.: 09/529,390

(22) PCT Filed: Aug. 27, 1999

(86) PCT No.: PCT/EP99/06299

§ 371 Date: Jun. 19, 2000

§ 102(e) Date: Jun. 19, 2000

(87) PCT Pub. No.: WO00/12999

PCT Pub. Date: Mar. 9, 2000

Related U.S. Application Data (60) Provisional application No. 60/098,247, filed on Aug. 28, 1998.

(51) Int. Cl.[7] .................................................. H01L 21/66
(52) U.S. Cl. .................................. 438/16; 438/7; 438/14
(58) Field of Search ................................ 438/16, 14, 7, 438/404

(56) References Cited

U.S. PATENT DOCUMENTS 5,002,399    3/1991    Akinc et al. .
5,342,580    8/1994    Brenner .

FOREIGN PATENT DOCUMENTS 0 779 507 A1    6/1997    (EP) .

OTHER PUBLICATIONS

S. Zangooie, et al "Water interaction with thermally oxidized porous silicon layers." J. of the Electrochem. Soc. vol. 144, No. 11, pp. 4027–4035, Nov. 1997.*

Petterson et al., "Porosity depth profiling of thin porous silicon layers by use of variable–angle spectroscopic ellipsometry: a porosity graded–layer model," Applied Optics 37(19):4130–4136 (1998).

* cited by examiner

Primary Examiner—Caridad Everhart
(74) Attorney, Agent, or Firm—McDonnell Boehnen Hulbert & Berghoff (57) ABSTRACT

The present invention is related to an apparatus and a non-destructive method for determining the porosity of an element, particularly a thin film, formed on a substrate, said substrate being positioned in a pressurized chamber, said chamber being at a predetermined pressure and at a predetermined temperature. According to this method a gaseous substance like e.g. toluene vapor is admitted in said chamber and after a predetermined period of time the porosity of the thin film is determined by means of at least on ellipsometric measurement. Particularly, the optical characteristics resulting from this in-situ ellipsometry are used to determine the amount of gaseous substance condensed in the pores of the film. These amounts are used to calculate the porosity of the film.

14 Claims, 6 Drawing Sheets

APPARATUS AND METHOD FOR DETERMINING POROSITY

This appln is a 371 of PCT/EP99/06299 filed Aug. 27, 1999, which claims; benefit of Prov. No. 60/098,247 filed Aug. 28, 1998.

FIELD OF THE INVENTION

The present invention is related to an apparatus and a non-destructive method for determining the porosity of a layer or part of a layer formed on a substrate. The porosity and particularly the pore size distribution defines the mechanical, thermal and chemical properties of the porous materials. For example, by knowing the pore size distribution, one has a clear indication of the compatibility of this layer with the manufacturing process of integrated circuits or liquid crystal displays.

BACKGROUND OF THE INVENTION

The ongoing miniaturization in integrated circuits with increased complexity and multilevel metal layers and the focus on increasing speed of these circuits has increased the demand for low permittivity materials, particularly for use as intermetal dielectric layers. Conventionally, metal interconnects, mostly aluminum layers, with silicon dioxide as intermetal dielectric are used, but this conventional solution will not be able to meet the stringent specifications resulting from the above mentioned trends. Therefore, to avoid that the larger portion of the total circuit delay is caused by the resistance and capacitance of the interconnect system, the permittivity of the dielectric used has to be reduced. This is stated in numerous publications, e.g. in Table 1 of R. K. Laxman, "Low ∈ dielectric: CVD Fluorinated Silicon Dioxides", Semiconductor International, May 1995, pp. 71–74. Therefore miniaturization has lead to an intensified search for new low K materials. A low ∈ material, a low K material and a material with a low permittivity are all alternative expressions for a material with a low dielectric constant, at least for the purposes of this disclosure.

Part of the search for new low K materials has been directed to changing the properties of silicon dioxide as deposited. Besides the focus has been on changing the properties of silicon oxide, there is an ongoing search for new low K materials. Among these new materials are the organic spin-on materials, having a K value in the range from 2.5 to 3, and the inorganic low-K materials as e.g. xerogels having a K value typically lower than 1.5. An important characteristic of these new materials is their porosity, i.e. the volumes of the pores as well as the pore size distribution. The relative pore volume directly defines the permittivity value and can be estimated by measurement of the dielectric constant using spectroscopic ellipsometry and porosity/density simulation as e.g. in T. Ramos et al., "Low-Dielectric Constant Materials", Mater. Res. Soc. Proc. 443, Pittsburgh, Pa. 1997, p.91. However, it is much more difficult to measure the pore size distribution. The pore size distribution defines mechanical, thermal and chemical properties of the porous materials. Therefore, by knowing the pore size distribution, one has a clear indication of the compatibility of the material with the manufacturing process of integrated circuits. If the pores are open, information about the pore size distribution can be obtained by adsorption porometry.

Adsorption porometry is based on the well-known phenomenon of hysteresis loop that appears in the processes of capillary condensation and desorption of vapour out of porous adsorbents. The theory of capillary condensation, as in S. J. Gregg and S. W. Sing, "Adsorption, Surface Area and Porosity", Acad. Pr., NY, 1982, explains the appearance of hysteresis by the change in the equilibrium vapour pressure above the concave meniscus of the liquid. Vapour can condense in the pores of a solid substrate even if its relative pressure is below unitary value, i.e. there is condensation even when the vapour pressure is less than the atmospheric pressure. Dependence of the relative pressure on the meniscus curvature is described by Kelvin equation:

$$\ln(P/P_0) = -2\gamma V_L/(r_m RT),$$

where $P/P_0$ is the relative pressure of the vapour in equilibrium with the liquid, the surface of the liquid being a meniscus with the curvature radius $r_m$; $\gamma$ and $V_L$ are the surface tension and molar volume of the liquid adsorbate, respectively. The curvature radius $r_m$ is close to the pore radius. Adsorption-desorption hysteresis appears if the radius of curvature of the meniscus of the condensing liquid is changed as a result of adsorption. Every $P/P_0$ value corresponds to a definite $r_m$. Only spheroidal menisci are formed during desorption, while adsorption results in either spheroidal or cylindrical menisci. Because of this, it is more convenient to use desorption isotherms to determine the effective size of pores equivalent to cylindrical ones.

A method of wide application is adsorption porometry with the use of liquid nitrogen as in S. J. Gregg et al., "Adsorption, Surface Area and Porosity", Acad. Pr., NY, 1982. This state-of-the-art method is however only applicable when analyzing large samples because this method is based on direct weighing of the samples during the vapour adsorption and desorption. Therefore, this destructive method is inappropriate for analyzing thin films formed on a substrate. In some cases, in order to characterize the pore size distribution using this state-of-the-art method, it is necessary to damage the films of several tens of substrates. Moreover, the very low temperature which is required for nitrogen porometry also creates additional problems.

SUMMARY OF THE INVENTION

In an aspect of the invention a method is disclosed for determining the porosity of an element formed on a substrate, said substrate being positioned in a pressurized chamber, said chamber being at a predetermined pressure and at a predetermined temperature, said method comprising the steps of:

admitting a gaseous substance in said chamber; and determining after a predetermined period of time the porosity of said element by means of at least on ellipsometric measurement.

For instance, the gaseous substance can be a vapour, or a gas or a mixture thereof. An appropriate gaseous substance is a substance which is at a predetermined temperature and a predetermined pressure (preferably at a pressure below the equilibrium vapour pressure of said gaseous substance) present both as a gaseous substance as well as condensed gaseous substance. The gaseous substance is preferably selected such that the interaction between the condensed gaseous substance and the thin film is as limited as possible. More preferably, said predetermined temperature is room temperature. An example of said element formed on said substrate is a thin film, particularly a thin film of an organic or inorganic material, preferably, with a low dielectric constant.

In an embodiment of the invention, said predetermined period of time is chosen such that in said chamber equilibrium is established between said gaseous substance and the condensed form of said gaseous substance.

In an embodiment of the invention a method is disclosed for determining the porosity of an element formed on a substrate comprising the steps of:

selecting a gaseous substance being admissible to an exposed surface of the element formed on the substrate, said substrate being positioned in a pressurized chamber at a predetermined constant temperature;

setting the pressure in the chamber to a first predetermined value;

admitting said gaseous substance in said chamber, the temperature of the gaseous substance being substantially identical to said predetermined constant temperature;

after a predetermined period of time measuring the value of the pressure in the chamber and performing an ellipsometric measurement to determine the optical characteristics of the element;

changing the pressure in the chamber in a stepwise manner, whereby after each step and after a predetermined period of time the optical characteristics are determined by means of an ellipsometric measurement, to thereby determine an adsorption-desorption isotherm; and calculating the porosity using at least the measured optical characteristics and the adsorption-desorption isotherm.

In another aspect of the invention an apparatus is disclosed for determining the porosity of an element formed on a substrate, said apparatus comprising:

a pressurized chamber in which said substrate is positionable;

a temperature control element for fixing the temperature in said chamber at a predetermined value;

a pump for changing the pressure in said chamber;

a supply for admitting a gaseous substance;

an ellipsometer for determining the optical characteristics of said element;

at least a first controllable component and at least a second controllable component, said first component being positioned between said pump and said chamber and allowing a precise control of the pressure in the chamber, said second component being positioned between said supply and said chamber and allowing a precise control of the flow of said gaseous substance into said chamber; and wherein the porosity is calculated from said optical characteristics. Particularly the inner walls of said chamber are composed of a material with a porosity which is substantially lower than the porosity of the element to be analysed.

In another embodiment of the invention, the apparatus can further comprise a control element and a recording element. The control element controls the first and second component. The recording element allows to record the pressure in the chamber, the optical characteristics and the adsorption-desorption curve thereby enabling the calculation of the porosity of the element.

In another embodiment of the invention an apparatus is disclosed for determining the porosity of an element formed on a substrate wherein said second controllable component is a microvalve being composed of at least a first material and a second material, said first material being conductive, said second material being elastic and wherein said first material and said second material have a substantially different thermal expansion coefficient.

DETAILED DESCRIPTION OF THE INVENTION

In relation to the appended drawings the present invention is described in detail in the sequel. Several embodiments are disclosed. It is apparent however that a person skilled in the art can imagine several other equivalent embodiments or other ways of executing the present invention, the spirit and scope of the present invention being limited only by the terms of the appended claims.

Figure 1:
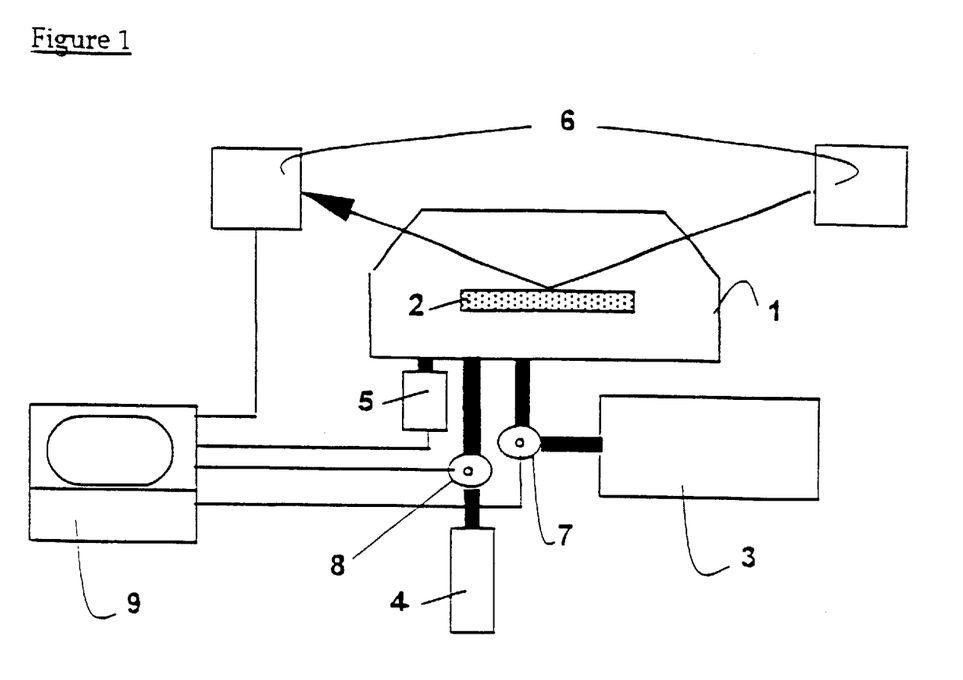
FIG. 1 depicts, according to an embodiment of the invention, a schematic diagram of an apparatus for determining in a non-destructive manner the porosity of an element formed on a substrate.
Figure 2:
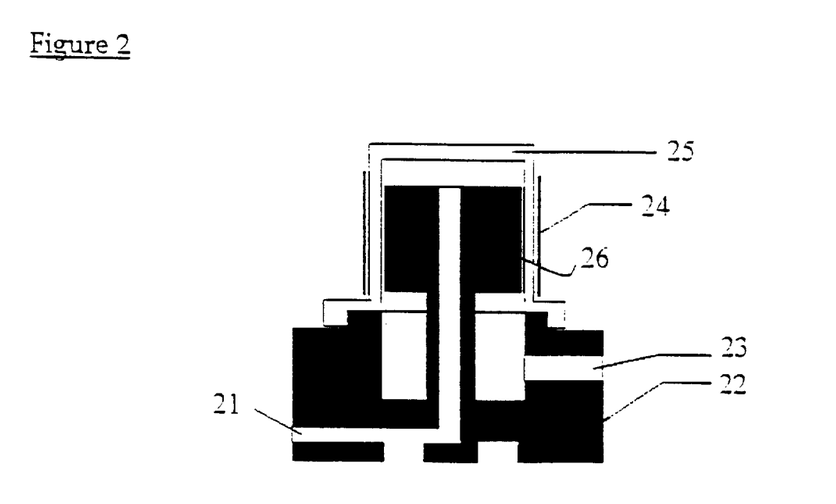
FIG. 2 depicts, according to an embodiment of the invention, a schematic diagram of a controllable microvalve used to control the flow of toluene vapour in a chamber.

In an embodiment of the invention an apparatus is disclosed for determining the porosity of an element formed on a substrate, said apparatus comprising:

a pressurized chamber (1) in which said substrate (2) is positionable;

a temperature control element for fixing the temperature in said chamber at a predetermined value;

a pump (3) for changing the pressure in said chamber;

a supply (4) for admitting a gaseous substance;

a manometer (5) for measuring the pressure in said chamber;

an ellipsometer (6) for determining the optical characteristics and particularly the refractive index and the thickness of said element;

at least a first controllable component (7) and at least a second controllable component (8), said first component being positioned between said pump and said chamber and allowing a precise control of the pressure in the chamber, said second component being positioned between said supply and said chamber and allowing a precise control of the flow of said gaseous substance into said chamber; and wherein the porosity is calculated using at least values from said refractive index and said thickness element. Particularly, preferably said second component is a microvalve as depicted in FIG. 2. A gaseous substance is admitted into an input cavity (21) formed in the microvalve. The major part of the microvalve is composed of a conductive material (22). Particularly, preferably a non-corrosive metal, e.g. non-corrosive steal, is used. The input cavity is separated from the output cavity (23) by means of a thin film (25) of an elastic material with a thermal expansion coefficient being substantially different from the thermal expansion coefficient of said conductive material. Particularly, said elastic material can be teflon. This thin film is thermally connected to a heating element (24). If the temperature of the thin film increases, then said film expands and a narrow channel (26) is created between said thin film and said conductive element. So, the width of the channel is dependent on the temperature and can be controlled by controlling the heating element. Once said channel is created, the gaseous substance can flow from the input cavity to the output cavity, said output cavity being connected to the pressured chamber of the apparatus of the present invention. The flow being dependent on the width of the channel. In an alternate embodiment of the invention, said second component is a commercial available microvalve.

In another embodiment of the invention, as in FIG. 1, the apparatus can further comprise a control element and a recording element (9). The control element controls the first and second component. The recording element allows to record the pressure in the chamber, the refractive index of the element, the thickness of the element and the adsorption-desorption curve thereby enabling the calculation of the porosity of the element.

In another embodiment of the invention an apparatus and a method is disclosed for determining the porosity, particularly the pore size distribution, of an element formed on a substrate. Examples thereof are thin films formed on a substrate. The substrate can be any conductive, semiconductive or insulating wafer or plate like a silicon wafer or a glass plate. This method is a non-destructive method applicable on wafer scale and based on the determination of an adsorption-desorption hystereris loop at a predetermined constant temperature and in-situ ellipsometry.

A first requirement to determine an adsorption-desorption isotherm is the selection of an appropriate gaseous substance. A gaseous substance can be a vapour, or a gas or a mixture thereof. An appropriate gaseous substance is a substance which is at a predetermined temperature present both as a gaseous substance as well as condensed gaseous substance, particularly at a pressure below the equilibrium vapour of said gaseous substance at said predetermined temperature. The condensed gaseous substance is intended to fill the open pores in the thin film being the element formed on the substrate. Further, in order to determine the adsorption-desorption isotherm, the substrate with the thin film thereon has to be introduced in a pressurized chamber at a predetermined value of the pressure. The gaseous substance is admitted into the chamber and condenses partly into the thin film dependent upon pressure and temperature. Once equilibrium is established between gaseous and condensed form, the amount of gaseous substance condensed into the pores of the film can be determined with high accuracy.

The gaseous substance is preferably selected such that the interaction between the condensed gaseous substance and the thin film is as limited as possible. Furthermore the gaseous substance is preferably admissible into the pressurized chamber at room temperature being 21 degrees Celsius and has a condensation temperature between 25 and 100 degrees Celsius and an equilibrium pressure between 10 and 100 Torr. In the latter case the measurements can be performed at room temperature. Previous studies, as in M. R. Baklanov, F. N. Dultsev and S. M. Repinsky, Poverkhnost', 11, 1445 (1988) (Rus.), showed that the vapour of some organic solvents can be used as a gaseous substance. Non-polar solvents without permanent dipole moment are preferred. According to the examples mentioned in this embodiment, toluene is selected among the solvents. In other words, toluene in vapour phase is used as a gaseous substance. One of the reasons for this choice is that toluene is often used as an adsorbate to determine the specific surface area. As a consequence, the reference data for this solvent are available.

To determine the porosity of an element, particularly a thin film, formed on a substrate an apparatus (FIG. 1) is used, comprising:

a pressurized chamber wherein said substrate can be positioned;

a temperature control element for fixing the temperature in said chamber at a predetermined value;

a pump for changing the pressure in said chamber;

a supply for admitting a gaseous substance;

a manometer for measuring the pressure in said chamber;

an ellipsometer for determining the refractive index and the thickness of said element;

a control element for controlling at least a first microvalve and at least a second microvalve, said first microvalve being positioned between said pump and said chamber and allowing a precise control of the pressure in the chamber, said second microvalve being positioned between said supply and said chamber and allowing a precise control of the flow of said gaseous substance into said chamber;

a recording element allowing to record the pressure in the chamber, the refractive index of the element, the thickness of the element and the adsorption-desorption curve thereby enabling the calculation of the porosity of the element. Particularly, in-situ ellipsometry is used to determine the amount of the gaseous substance adsorbed/condensed in the film amongst others from the change of the refractive index, n, and the film thickness, d. This ellipsometric porometry, according to the method of the invention, is based on the relation between the refractive index and density of the film as described by the Lorentz-Lorenz equation.

Further according to this embodiment of the invention, the apparatus and the method of the present invention are by means of example applied for the determination of the porosity and particularly the pore size distribution in a silicon dioxide film, deposited by means of low temperature/ low pressure chemical vapour deposition (CVD) on a silicon wafer, and in a xerogel film formed on a silicon wafer by means of a sol-gel technique. A silicon wafer with the film thereon is positioned into the pressurized chamber of the apparatus at room temperature. The pressure is set to a first predetermined value. This value is substantially below the equilibrium vapour pressure of toluene at room temperature ($P_0$). Then toluene vapour as gaseous substance is admitted into the pressurized chamber at room temperature. The temperature of the toluene vapour is substantially identical to room temperature. After a predetermined period of time, the pressure in the chamber is measured using a manometer and also ellipsometric measurements are performed. This predetermined period of time is chosen such that equilibrium is reached in the chamber between the gaseous substance, being toluene vapour, and toluene condensed into the open pores of the film. Thereafter, the pressure in the chamber is changed in a stepwise manner, whereby at each step, after a predetermined period of time, the pressure (P) is measured in the chamber and ellipsometric measurements are performed. The measured values are recorded using the recording element of the apparatus. Particularly, the pressure is varied from an initial value of the relative pressure (P/P$_0$) of about zero to a value of the relative pressure of about 1 and backwards to thereby record an adsorption-desorption isotherm.

Figure 3:
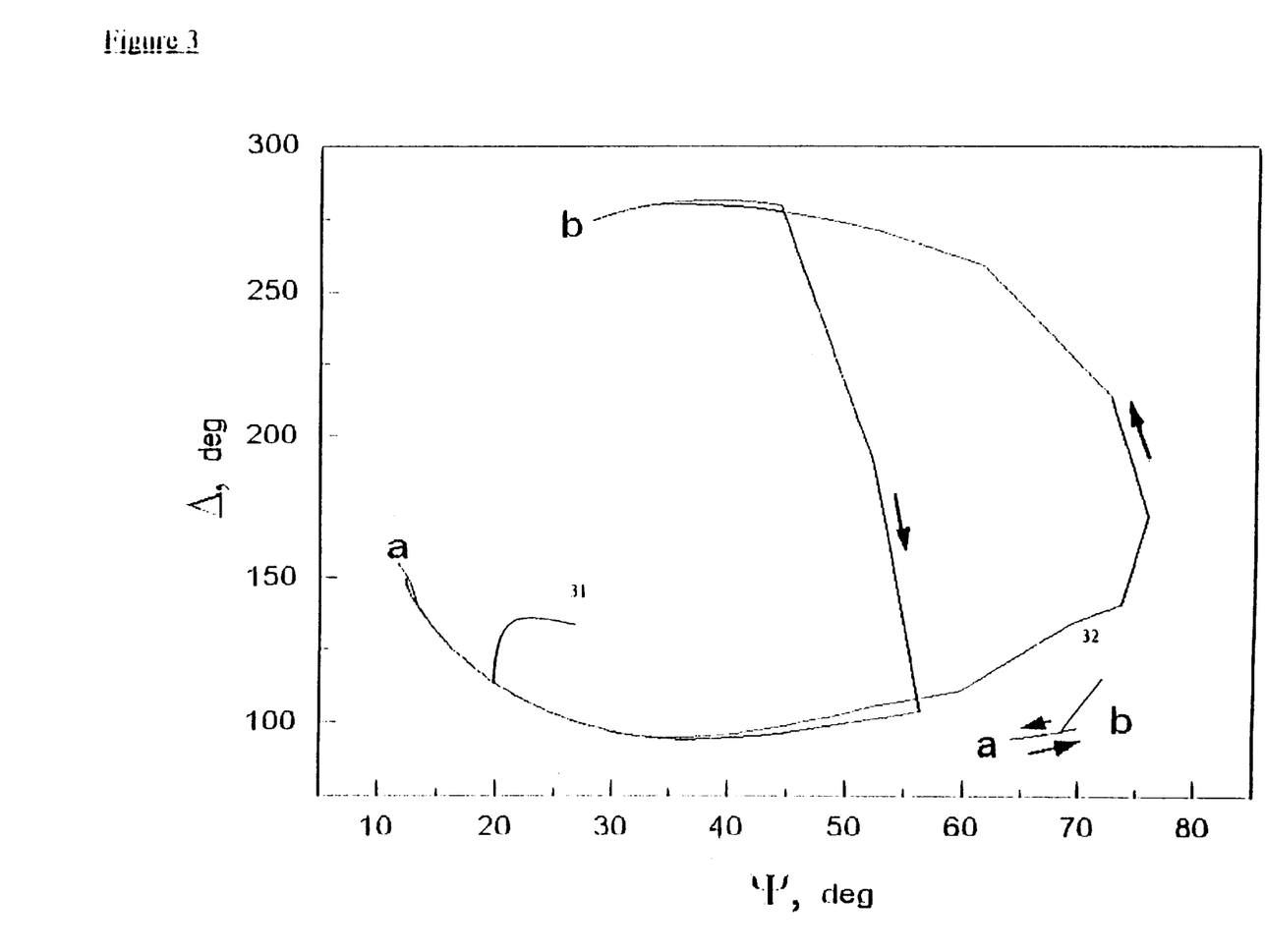
FIG. 3 depicts, according to an embodiment of the invention, the polarisation angles measured using an ellipsometer both for an $SiO_2$ (32) and a xerogel (31) film during the adsorption/desorption cycle of the toluene vapour. Point a corresponds to a relative pressure $P/P_0=0$; point b corresponds to a relative pressure $P/P_0=1$.

The measurement technique of ellipsometry is reviewed in "The Optics Source Book", Editor Sybil P. Parker, 1988, McGraw-Hill. The ellipsometric measurements are performed using ellipsometry at a wavelength of 632.8 nm. Ellipsometry means a reflection experiment using polarized radiation to get the ratio of the reflections in the selected directions perpendicular and parallel to the plane of incidence and the difference of phase associated with the reflection. From these data result the ellipsometric angles. Knowing these angles the refractive index as well as the thickness of the film (element) can be determined. So, particularly according to this embodiment of the invention, the change of the ellipsometric angles versus the pressure (P) in the chamber are recorded. The change of the ellipsometric angles Δ and Ψ during the toluene adsorption and desorption is shown in FIG. 3 both for the xerogel film (31) as for the silicon dioxide film (32). The arrows show how the ellipsometric angles are changed when the relative pressure of toluene vapour is varied from zero to unit and back to zero. The initial point corresponds to the zero relative pressure (point a) and the final one to the relative pressure equal to unit (point b). The dependence has been recorded for the angle of light incidence on the sample equal to 70°. One can see that for the CVD SiO$_2$ the change of the ellipsometric characteristics is relatively small. These changes are defined only by change of the refractive index. However, a change of the angle Ψ equal to 10 degrees is definitely big enough to carry out reliable data analysis (the sensitivity of the ellipsometer is better than 0.01 degree). For the xerogel film a huge change of the ellipsometric characteristics was observed. In order to interpret these data, simulations were performed with several reasonable optical models which could provide a valuable description of the experimental data. It was found that both the film thickness and porosity are responsible for the scale of the change of the ellipsometric characteristics. The best agreement between the experimental curve and the calculated one was achieved with a model which assumed that the film thickness (d) was changed insignificantly (within 10%). The major changes were related to the change of the refractive index (n).

The values of the porosity of the SiO$_2$ and xerogel films calculated using the spectroscopic ellipsometry of the present invention were about 20% and about 70%, respectively. The CVD SiO$_2$ and xerogel film thickness were about 300 nm and about 500 nm, respectively. These pore size distribution data calculated from the ellipsometric measurements were compared with results obtained with microbalance porometry. By using a quartz crystal microbalance technique, as in M. R. Baklanov, L. L. Vasilyeva, T. A. Gavrilova, F. N. Dultsev, K. P. Mogilnikov and L. A. Nenasheva, Thin Solid Films, 171, 43(1989), adsorption porometry measurements were performed on thin films, deposited on a quartz resonator, with a sensitivity of 10$^{-8}$ g/Hz. The CVD SiO$_2$ films were deposited on top of a quartz resonator preliminary calibrated for this purpose. So, in fact this microbalance method is a destructive method because the substrate with the film thereon can not be used for further processing. Therefore, this method can not be used for films deposited onto a silicon substrate.

Figure 4A:
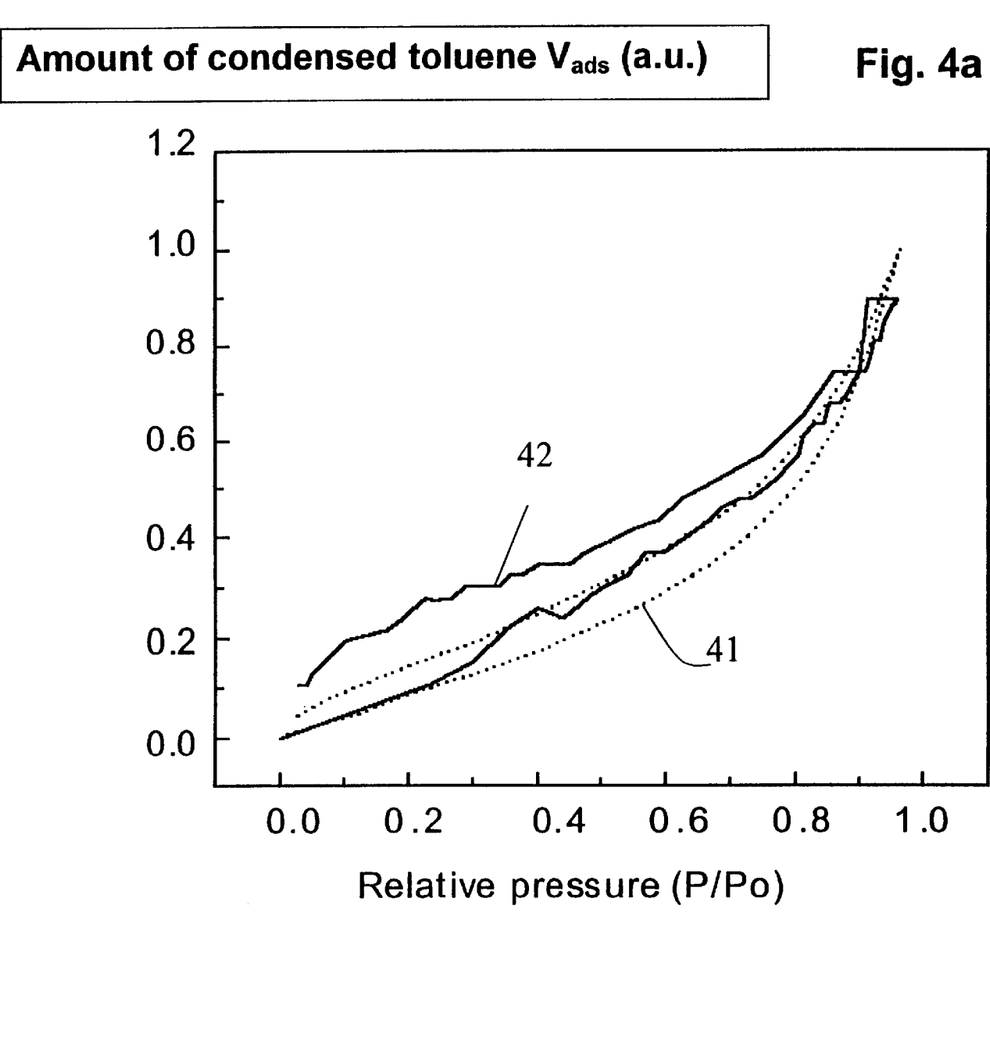
FIG. 4a depicts an adsorption-desorption isotherm of an $SiO_2$ film with a porosity of 20% using a microbalance method (41) and the method according to an embodiment of the present invention (42).

Further, according to the examples in this embodiment, FIG. 4a shows the dependence of the amount of gaseous substance, i.e. toluene, condensed in the CVD SiO$_2$ film as calculated from the ellipsometric measurements according to the method of the invention (42) and the relative amount of adsorbed/condensed toluene vapour obtained by quartz crystal microbalance on relative pressure (41). In order to be able to perform the microbalance measurements, a similar SiO$_2$ film is deposited by CVD under identical conditions as the SiO$_2$ film of the example on top of a quartz crystal resonator. Furthermore, in order to be able to make a comparison between the results obtained using the method of the present invention and the microbalance method, all the data are normalized and presented in relative units. As depicted in (FIG. 4b) both methods give close pore size distribution. The ellipsometric measurements according to the method of the present invention give somewhat overestimated values. However, in numerous porosity measurements which have been performed the observed difference never exceeded 10%.

Figure 4B:
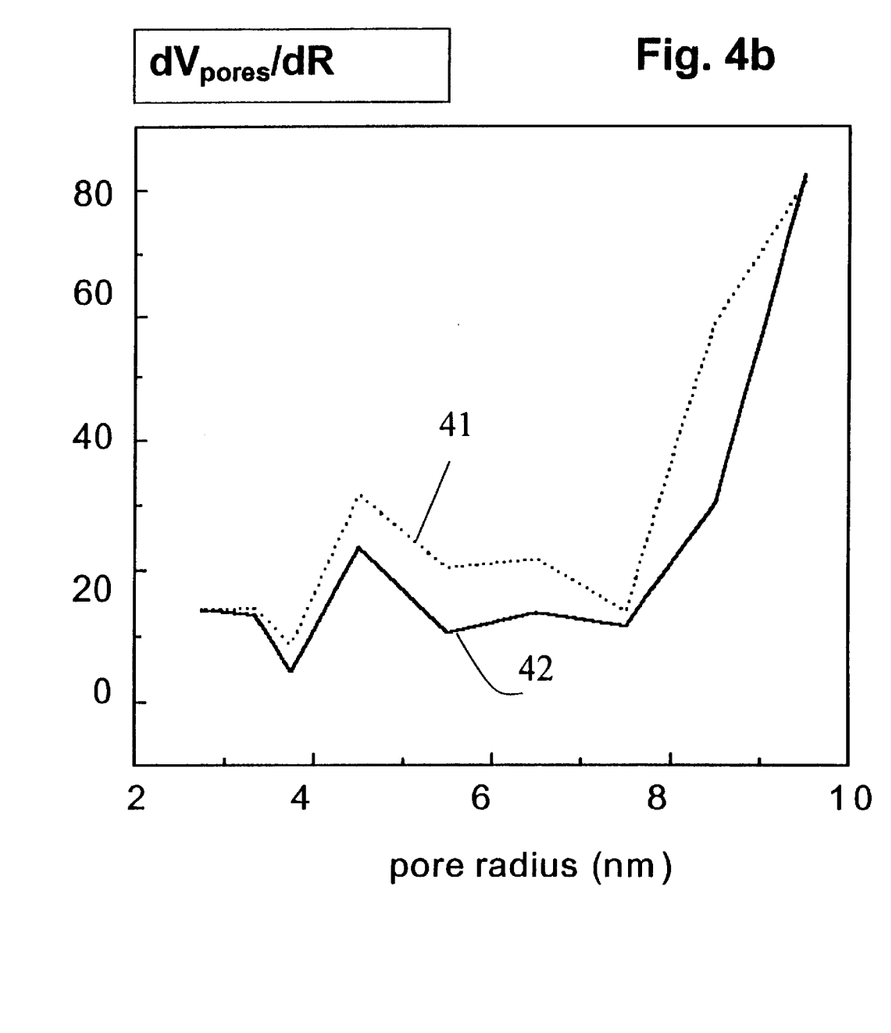
FIG. 4b depicts the pore size distribution of an $SiO_2$ film with a porosity of 20% using a microbalance method (41) and the method according to an embodiment of the present invention (42).
Figure 5A:
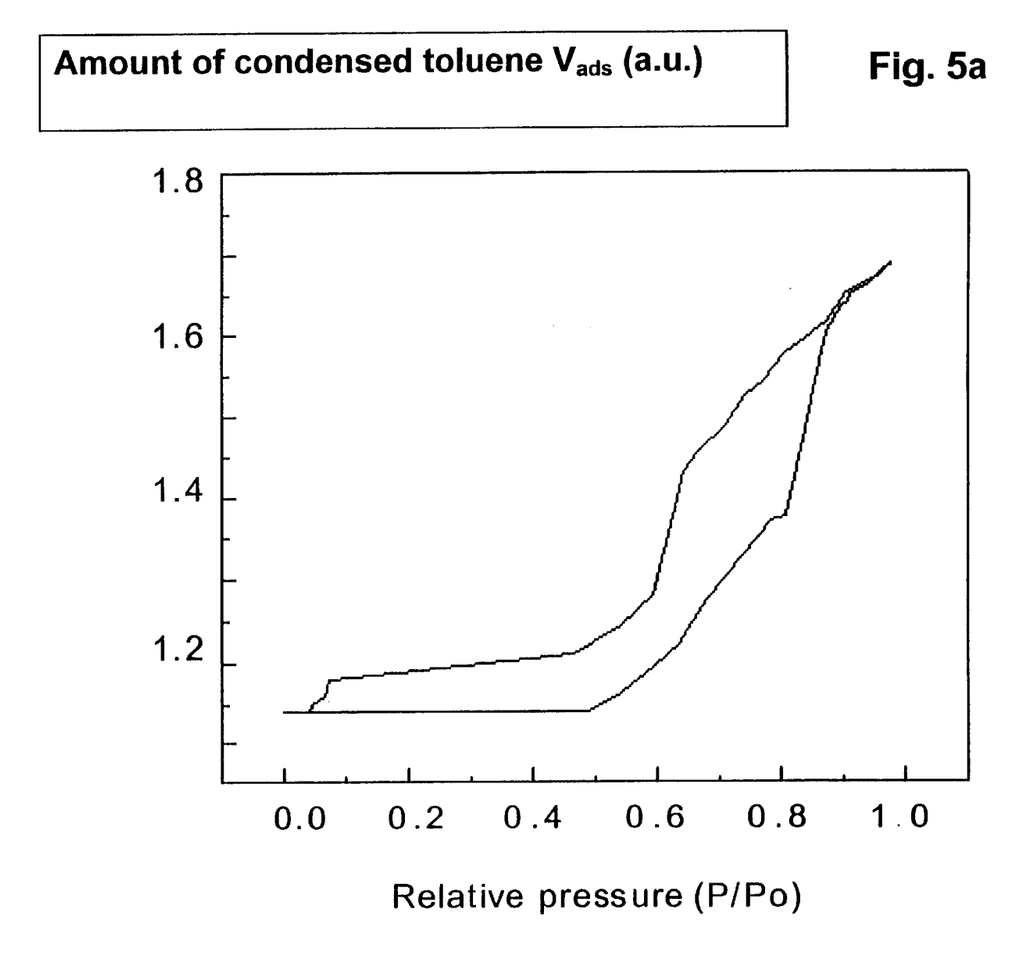
FIG. 5a depicts an adsorption-desorption isotherm of a xerogel film with a porosity of 70% using the method according to an embodiment of the present invention.
Figure 5B:
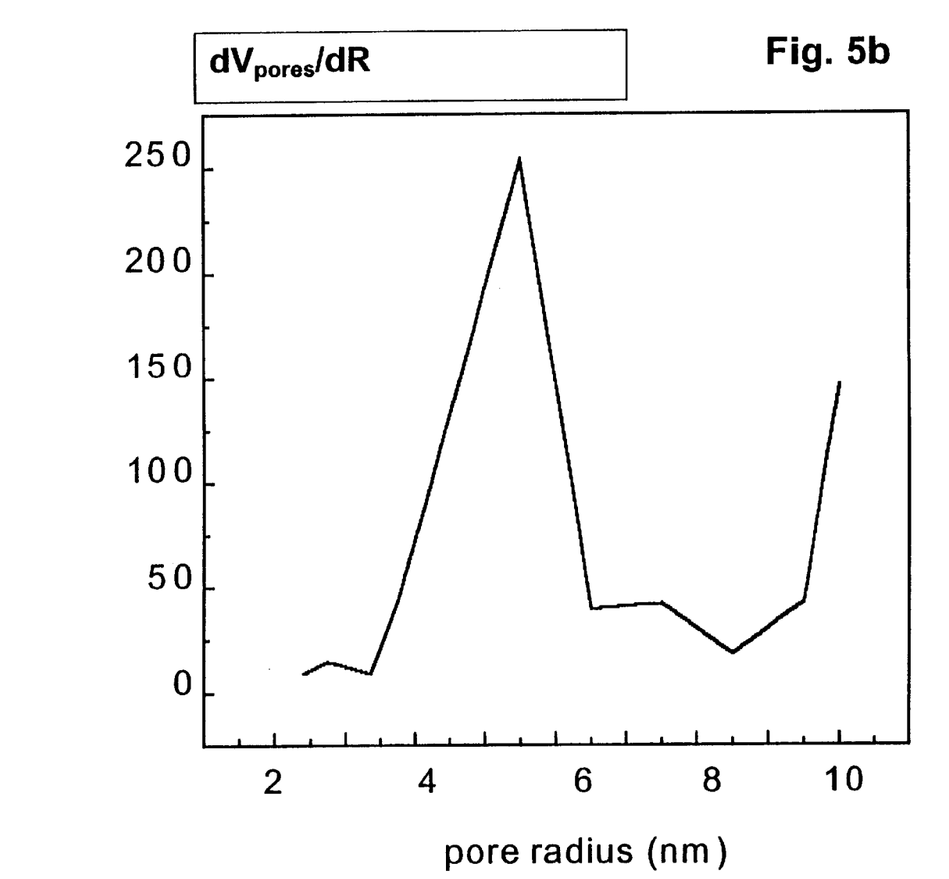
FIG. 5b depicts the pore size distribution of a xerogel film with a porosity of 70% using the method according to an embodiment of the present invention.

Analogous to FIG. 4, FIG. 5a depicts the adsorption-desorption isotherm and FIG. 5b the pore size distribution but for the xerogel film instead of the SiO$_2$ film. These data show that the xerogel film contains mainly mesopores with radii between 4 and 6 nm. The computer simulation showed that the change of the ellipsometric characteristics during the vapour adsorption is described by a single-layered optical model. This means that the "wetting" of the xerogel films occurs uniformly. Therefore the results of the adsorption-desorption experiments and their analysis allow to conclude that pores in the film are interconnected.

While the invention has been shown and described with reference to preferred embodiments, it will be understood by those skilled in the art that various changes or modifications in form and detail may be made without departing from the scope and spirit of this invention as defined in the attached claims.

What is claimed is:

1. A method for determining porosity of an element formed on a substrate using a gaseous substance, said substrate being positioned in a pressurizable chamber at a chamber temperature, said method comprising the steps of:
   setting said chamber to a modified pressure, the modified pressure being less than equilibrium vapor pressure of said gaseous substance at the chamber temperature;
   admitting a gaseous substance in said chamber;
   performing at least one ellipsometric measurement to determine optical characteristics at said modified pressure and at said chamber temperature; and
   calculating said porosity of said element.

2. A method as recited in claim 1, wherein the gaseous substance is a substance being present both as a gaseous substance as well as condensed gaseous substance at said modified pressure and said chamber temperature.

3. A method as recited in claim 2, wherein after admitting said gaseous substance, a period of time is allowed to elapse before the ellipsometric measurement step such that in said chamber, equilibrium is established between said gaseous substance and the condensed form of said gaseous substance.

4. A method in accordance with claim 1, wherein said gaseous substance is admissible to an exposed surface of the element formed on the substrate,
   wherein the gaseous substance is at a temperature being substantially identical to said chamber temperature, further comprising the steps of:

after a period of time measuring at least one value of pressure in the chamber and performing the ellipsometric measurement to determine the optical characteristics of the element;

changing the pressure in the chamber, whereby after each step the optical characteristics are determined by means of an ellipsometric measurement, and wherein the step of calculating the porosity includes using at least the measured optical characteristics.

5. A method according to claim 1, wherein the gaseous substance is a non-polar solvent.

6. A method according to claim 4, wherein the step of changing the pressure in the chamber includes changing the pressure in the chamber in a step-wise manner.

7. A method in accordance with claim 1, wherein said gaseous substance is introduced to an exposed surface of the element formed on the substrate, wherein the gaseous substance is at a temperature being substantially identical to said chamber temperature, further comprising the steps of:

after a period of time measuring at least one value of pressure in the chamber and performing the ellipsometric measurement to determine the optical characteristics of the element;

changing the pressure in the chamber, whereby after each step the optical characteristics are determined by means of an ellipsometric measurement, and wherein the step of calculating the porosity includes using at least the measured optical characteristics.

8. A method according to claim 7, wherein the step of changing the pressure in the chamber includes changing the pressure in the chamber in a step-wise manner, and wherein after each step of changing the pressure in the chamber in a stepwise manner and after a period of time, the optical characteristics are determined by means of an ellipsometric measurement.

9. A method according to claim 6, whereby after each step of changing the pressure in the chamber in a stepwise manner and after a period of time, the optical characteristics are determined by means of an ellipsometric measurement.

10. A method for determining the porosity of an element formed on a substrate, the method comprising the steps of:

selecting a gaseous substance being admissible to an exposed surface of the element formed on the substrate, said substrate being positioned in a pressurized chamber at a constant temperature;

setting the pressure in the chamber to a first modified value;

admitting said gaseous substance in said chamber, the temperature of said gaseous substance being substantially identical to said constant temperature;

after a predetermined period of time measuring at least one value of the pressure in the chamber and performing an ellipsometric measurement to determine the optical characteristics of the element;

changing the pressure in the chamber in a stepwise manner, whereby after each step and after a period of time the optical characteristics are determined by means of an ellipsometric measurement, to thereby determine an adsorption-desorption isotherm; and calculating the porosity using at least the measured optical characteristics and the adsorption-desorption isotherm.

11. A method for determining porosity of an element formed on a substrate using a gaseous substance, said substrate being positioned in a pressurizable chamber at a chamber temperature, said method comprising the steps of:

modifying pressure in said chamber;

introducing a gaseous substance in said chamber;

performing at least one ellipsometric measurement to determine optical characteristics; and calculating said porosity of said element.

12. A method according to claim 11, wherein the step of modifying pressure in said chamber includes modifying the pressure to be less than equilibrium vapor pressure of said gaseous substance at the chamber temperature.

13. A method as recited in claim 12, wherein the gaseous substance is a substance being present both as a gaseous substance as well as condensed gaseous substance at said modified pressure and said chamber temperature.

14. A method as recited in claim 13, wherein after introducing said gaseous substance, a period of time is allowed to elapse before the ellipsometric measurement step such that in said chamber, equilibrium is established between said gaseous substance and the condensed form of said gaseous substance.

* * * * *

UNITED STATES PATENT AND TRADEMARK OFFICE
CERTIFICATE OF CORRECTION

PATENT NO.    : 6,319,736 B1
DATED         : November 20, 2001
INVENTOR(S)   : Baklanov et al.

It is certified that error appears in the above-identified patent and that said Letters Patent is hereby corrected as shown below:

Title page,
Item [73], please add the following (second) Assignee: -- Centre for Advanced Technologies TECHNOKOM, Novosibirsk (RU) --

Signed and Sealed this

Thirty-first Day of December, 2002

JAMES E. ROGAN
*Director of the United States Patent and Trademark Office*